United States Patent [19]

Inoue et al.

[11] Patent Number: 4,968,616
[45] Date of Patent: Nov. 6, 1990

[54] SUPEROXIDE DISMUTASE DERIVATIVES, METHOD OF PRODUCING SAME AND MEDICINAL USE OF SAME

[75] Inventors: Masayasu Inoue, 3-49-3, Ikeda, Kumamoto, Kumamoto; Tetsuya Ogino, Okayama City; Yoshimasa Morino; Masahiko Hirota, both of Kumamoto, all of Japan

[73] Assignees: Masayasu Inoue, Kumamoto; Kuraray Co., Ltd., Okayama, both of Japan

[21] Appl. No.: 49,349

[22] Filed: May 13, 1987

[30] Foreign Application Priority Data

May 16, 1986 [JP] Japan .................. 61-113095
Feb. 27, 1987 [JP] Japan .................. 62-45666

[51] Int. Cl.$^5$ .......................... C12N 9/96; C12N 9/02; A61K 37/48
[52] U.S. Cl. ...................... 435/188; 435/189; 424/94.3; 424/94.4
[58] Field of Search .............. 435/189, 188, 180; 424/94.4, 94.3; 530/815

[56] References Cited

U.S. PATENT DOCUMENTS

| | | | |
|---|---|---|---|
| 4,011,169 | 3/1977 | Diehl et al. | 252/95 |
| 4,563,349 | 1/1986 | Miyata et al. | 424/94 |
| 4,742,004 | 5/1988 | Hartman et al. | 435/70 |

*Primary Examiner*—Elizabeth C. Weimar
*Assistant Examiner*—Charles L. Patterson, Jr.
*Attorney, Agent, or Firm*—Burns, Doane, Swecker & Mathis

[57] ABSTRACT

Novel superoxide dismutase derivatives are provided in which the enzymatic activity of superoxide dismutase capable of decomposing superoxide, a substance harmful to living organisms, is for the most part maintained with the plasma half-life being significantly prolonged as compared with superoxide dismutase itself. They have pharmacological activities such as anti-inflammatory, anti-ischemic and cerebral edema-preventing activities. Also provided are a method of producing such superoxide dismutase derivatives and medicinal uses of them.

14 Claims, 8 Drawing Sheets

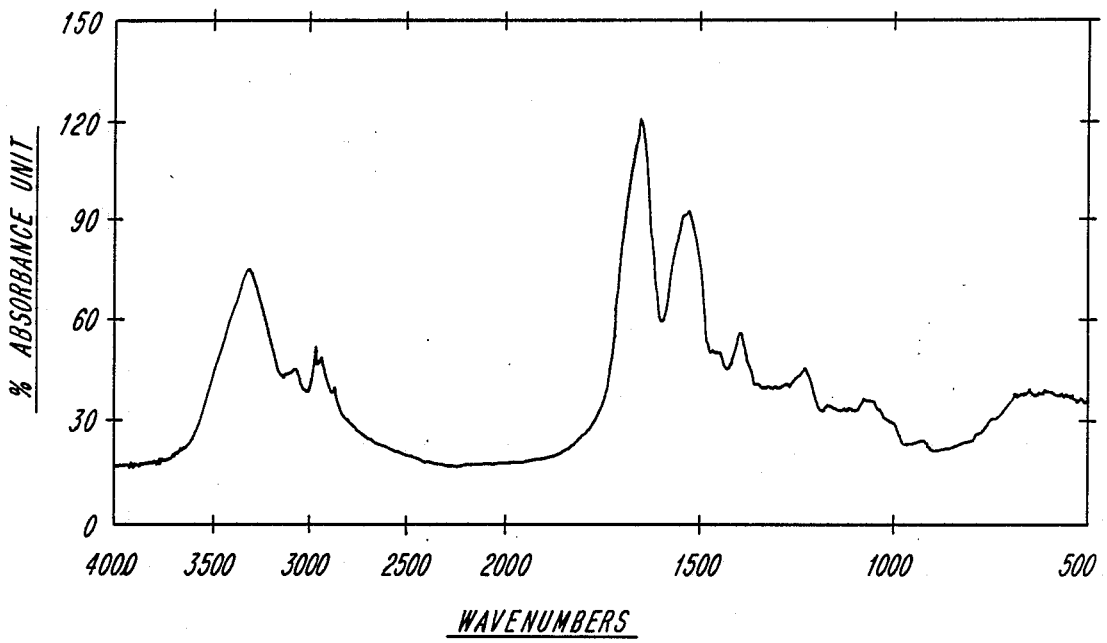
Fig. 4 (1)
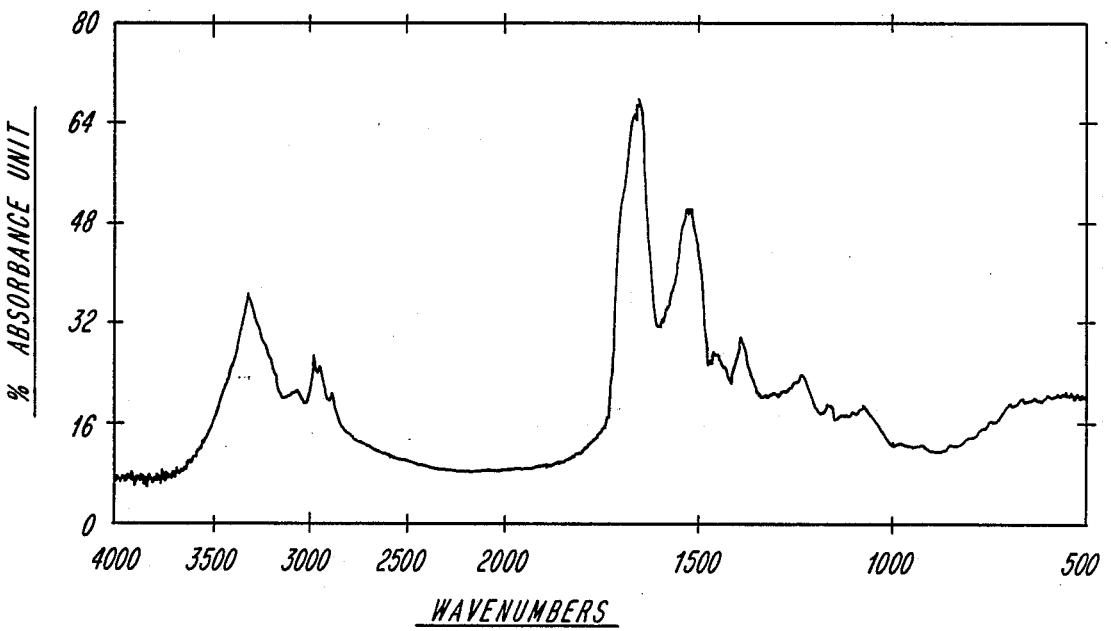
Fig. 4 (2)

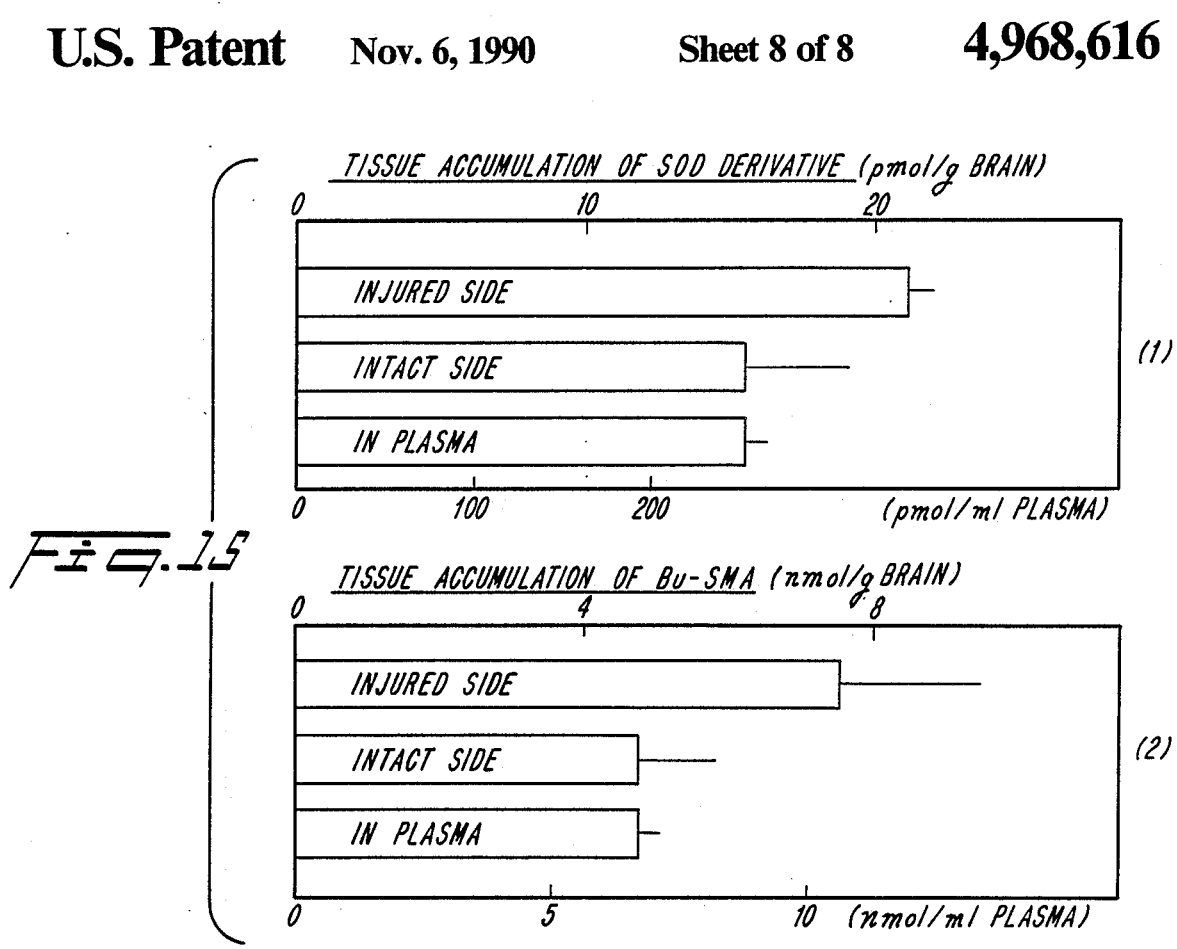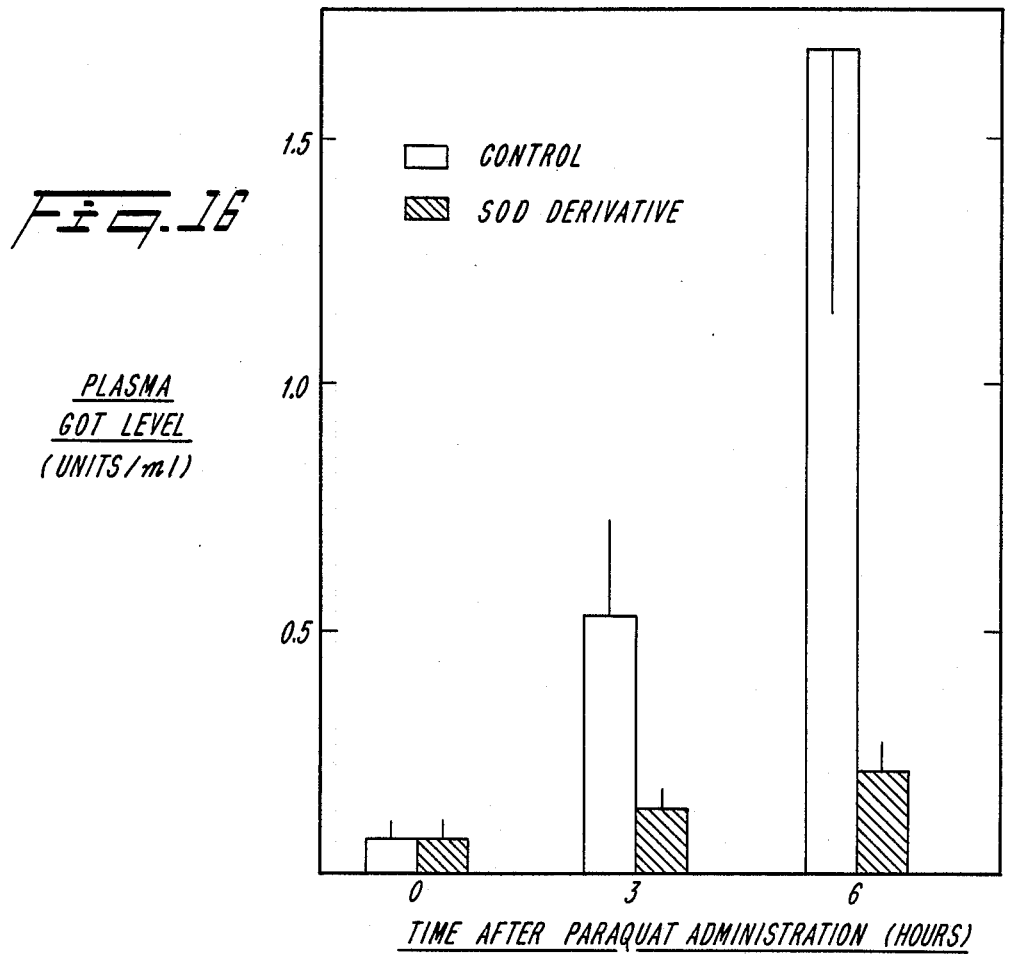

SUPEROXIDE DISMUTASE DERIVATIVES, METHOD OF PRODUCING SAME AND MEDICINAL USE OF SAME

BACKGROUND OF THE INVENTION

1. FIELD OF THE INVENTION

This invention relates to superoxide dismutase derivatives, a method of producing the same and medicinal use of the same.

2. DESCRIPTION OF THE PRIOR ARTS

Superoxide dismutase (hereinafter abbreviated as SOD) has been known so far as an enzyme occurring widely in living organisms, such as animals, plants and microbes, and decomposing superoxide which is harmful to living organisms. Recently, attempts have been made to use isolated SOD as an anti-inflammatory agent [Farumashia, 17, 411 (1981); Current Therapeutic Research, 16, 706 (1974)]. The use of SOD in the treatment of intractable radiation-induced colitis or in the prevention and treatment of gastric ulcer has also been studied [Jikken Igaku (Experimental Medicine), 4 (12), 39 (1986)].

As is clear from the results of a test example to be described later herein, human-type SOD is substantially lacking in anti-inflammatory activity and has very weak anti-ulcer activity.

It is said that the plasma half-life of intravenously administered SOD is only about 4 to 6 minutes; SOD is rapidly metabolized and excreted into urine. For prolonging the plasma half-life of SOD, attempts have been made to convert SOD to a giant molecule by modifying with Ficoll, polyethylene glycol or rat albumin. However, in the Ficoll- or polyethylene glycol-modified SOD, the enzymatic activity of SOD is markedly decreased, and the rat albumin-modified SOD has antigenicity. It has been reported that inulinmodified SOD has a reduced SOD activity as compared with unmodified SOD but has a much prolonged half-life in plasma [Japanese Kokai Tokkyo Koho No. 58-32826]. However, these modified SOD species have problems in their practical use for the above reasons or with respect to the decrease in tissue permeability due to the increase in molecular size.

It is an object of the invention to provide novel superoxide dismutase derivatives in which the enzymatic activity of SOD is substantially maintained with the plasma half-life being significantly prolonged as compared with SOD, without increasing the molecular size of SOD.

Another object of the invention is to provide novel and safe superoxide dismutase derivatives which have pharmacological activities such as anti-inflammatory, ischemic damage-preventing and cerebral edema-preventing activities.

A further object of the invention is to provide a method of producing the above-mentioned superoxide dismutase derivatives.

A still further object of the invention is to provide medicinal uses of said superoxide dismutase derivatives, for example as anti-inflammatory agents, protective agents against ischemic damages and agents for treating cerebral edema.

These objects as well as other objects and advantages of the present invention will become apparent to those skilled in the art from the following detailed description.

SUMMARY OF THE INVENTION

The invention provides superoxide dismutase derivatives of the formula $$[SOD][Z]_x$$

wherein [SOD] is a superoxide dismutase residue having 1 to 6 groups each derived from an amino group by removal of one hydrogen atom in lieu of the corresponding amino group or groups, [Z] is a monovalent copolymer residue composed of the following units:

(a) a group selected from the group consisting of

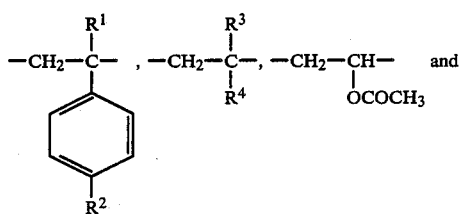

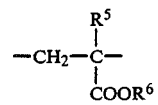

in which $R^1$, $R^3$ and $R^5$ each is a hydrogen atom or a methyl group, $R^2$ is a hydrogen atom, a chlorine atom, a bromine atom or a methyl group, $R^4$ is a hydrogen atom or an alkyl group containing 1 to 5 carbon atoms and $R^6$ is a methyl group or an ethyl group, (b) a group of the formula

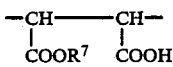

in which $R^7$ is a hydrogen atom or a residue of an alkanol containing 1 to 4 carbon atoms, of an ethylene glycol monoalkyl ether in which the alkyl group contains 1 to 4 carbon atoms or of a glycerol dialkyl ether in which each alkyl group contains 1 to 4 carbon atoms as resulting from removal of the hydroxyl group thereof, and (c) a group of the formula

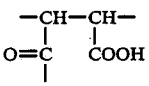

in which the carbonyl carbon atom is bound to [SOD] via a nitrogen atom of an amino group of [SOD], the copolymer residue having a weight-average molecular weight of 800 to 20,000, and x is an integer of 1 to 6 which corresponds to the number of the groups of [SOD] each derived from an amino group by removal of one hydrogen atom. [Hereinafter said superoxide dismutase derivatives are referred to as SOD derivatives.]

The invention also provides a method of producing the above SOD derivatives which comprises reacting SOD with a copolymer composed of the following units:

(a) a group selected from the group consisting of

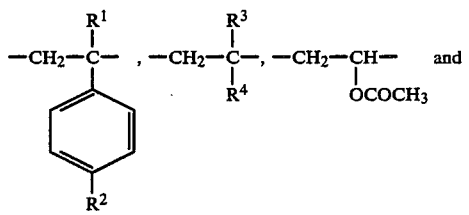

in which $R^1$, $R^2$, $R^3$, $R^4$, $R^5$ and $R^6$ are as defined above, (b) a group of the formula

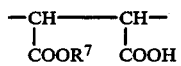

in which $R^7$ is as defined above, and (c) a group of the formula

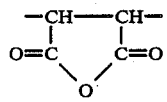

and having a weight-average molecular weight of 800 to 20,000, in an aqueous alkaline solution having pH of 7 to 11. [Hereinafter said copolymer is referred to as the copolymer for short.]

The invention further provides medicaments and pharmaceutical compositions which contain the SOD derivatives as active ingredients.

BRIEF DESCRIPTION OF THE DRAWINGS

In the accompanying drawings,

FIG. 4 (1) shows an IR spectrum of human erythrocyte SOD;

FIG. 4 (2) shows an IR spectrum of bovine erythrocyte SOD;

FIG. 15 (1) shows the accumulation of the SOD derivative in the right cerebral hemisphere with induced edema (injured side), in the left cerebral hemisphere (intact or control side), and in the plasma of rats;

FIG. 15 (2) shows the accumulation of Bu-SMA on the injured side, on the intact side, and in the plasma of the same rats as above; and FIG. 16 shows the relationship between the plasma GOT level and the time after paraquat administration in paraquat-treated mice given the SOD derivative and in paraquat-treated mice given no SOD derivative (control group).

DETAILED DESCRIPTION OF THE INVENTION

Figure 1:
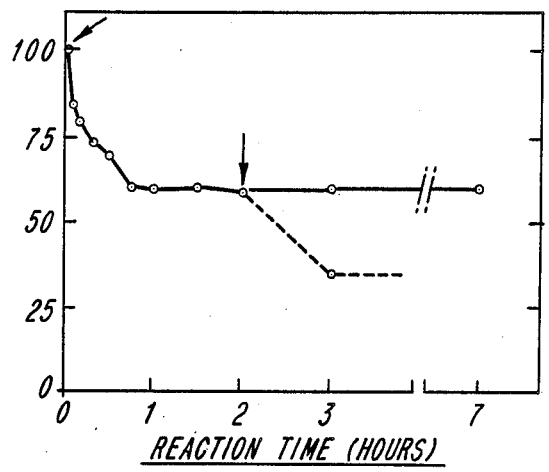
FIG. 1 shows the relationship between the reaction time and the percentage reduction of the TNBS-titratable amino group content in SOD in the case of the reaction of SOD and Bu-SMA (partially half butyl-esterified styrene-maleic anhydride copolymer; hereinafter the same shall apply) which is to be described in Synthesis Example 3.

The method of producing the SOD derivatives according to the invention is now described in detail.

The reaction of SOD and the copolymer is generally carried out by dissolving SOD in an aqueous solution of a salt such as sodium carbonate, sodium hydrogen carbonate, sodium acetate, sodium phosphate, etc. and adding, to the solution thus obtained, the copolymer in the form of a powder or a solution in an organic solvent such as dimethyl sulfoxide etc. It is necessary that the pH of the solution should be maintained at 7 to 11 during the reaction. When the pH is below 7, the solubility of the copolymer is low and the reaction does not proceed. When the pH is higher than 11, the enzymatic activity of SOD is lost and the SOD derivatives according to the invention cannot be obtained. The reaction temperature is to be selected preferably within the range of about 3° C. to about 50° C., more preferably within the range of 3° C. to 40° C. The reaction period should be selected depending on the reaction temperature and the mode of copolymer addition but generally amounts to 10 minutes to 3 hours. The copolymer is used in an amount of about 0.5 to 30 moles per mole of SOD. The number of copolymer molecules bound to each SOD molecule can be adjusted by varying the copolymer amount within the above range.

The reaction mixture thus obtained contains the SOD derivative, unreacted SOD, the copolymer, etc. Such reaction mixture is filtered, and the filtrate is subjected to gel filtration. If necessary, the thus obtained SOD derivative-containing effluent or eluate is subjected to hydrophobic chromatography and is then concentrated by ultrafiltration. The subsequent lyophilization gives the SOD derivative in a solid form.

In the above reaction, the amino group of SOD reacts with the maleic anhydride ring of the copolymer, whereby the SOD derivative is formed. Human-type Cu.Zn-SOD, for instance, contains 22 amino groups per molecule (in the case of human erythrocyte SOD or genetically engineered human-type SOD produced by yeast) or 24 amino groups per molecule (in the case of genetically engineered human-type SOD produced by *Escherichia coli*). The above reaction, in which any of the amino groups can react with one maleic anhydride ring of the copolymer, gives the SOD derivative with 1 to 6 molecules of the copolymer being bound to each molecule of SOD. Each molecule of the starting material copolymer generally contains, on an average, 0.5 to 2 maleic anhydride rings. When one of the maleic anhydride rings reacts with the amino group of SOD, the remaining maleic anhydride ring scarcely reacts with another amino group of SOD but tends to react with water to give the maleic acid-derived group

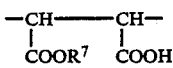

as a result of hydrolysis. Therefore, the above-mentioned constituent unit (b) of the SOD derivative includes that group in which $R^7$ is a hydride atom. When a partially half-esterified copolymer is used as the starting material, said constituent unit (b) includes not only that group in which the above maleic acid-derived group is half-esterified but also a small proportion of said maleic acid-derived group. There is the possibility that one molecule of the copolymer might react with a plurality of SOD molecules to give by-product compound in which a plurality of maleic anhydride rings of the copolymer each has been reacted with and bound to an amino group of each SOD molecule. Even when contaminated with a small proportion of such by-products, the SOD derivative according to the invention can be used as the active ingredient of medicaments and pharmaceutical compositions in accordance with the invention without any particular difficulties. However, in view of the current situation in which the compound to be used as a medicinally active ingredient should preferably have a definite single chemical structure, it is preferable to subject the SOD derivative, when it contains the above by-products in a fairly large amount, to gel filtration or some other treatment for removing the by-products and use the thus purified product as the medicinally active ingredient compound. The SOD derivative obtained in the above reaction is a mixture of SOD-copolymer coupling products differing in the number of copolymer molecules per SOD molecule. Therefore, the number x in the formula given above for representing the SOD derivative, which is provided by the invention, means the average number of copolymer molecules coupled with each SOD molecule. When the SOD derivative uniform in the number of copolymer molecules coupled with each SOD molecule is desired as the active ingredient compound, it is possible to obtain such SOD derivative by subjecting the SOD derivative obtained in the above manner to gel filtration or some other appropriate treatment. In the above reaction and in the subsequent treatment steps, the carboxyl group of the SOD derivative might possibly form an alkali metal salt or an ammonium salt. The SOD derivative according to the invention includes such SOD derivative containing the carboxyl group in a salt form as well.

The enzymatic activity of the SOD derivative tends to gradually decrease as the number of copolymer molecules per SOD molecule increases. Those SOD derivatives which contain 7 or more copolymer molecules per SOD molecule are too low in enzymatic activity, hence unsuitable for use as the medicinally active ingredient compounds. Those SOD derivatives that have 1 to 4 copolymer molecules coupled with each SOD molecule are preferred since they retain the enzymatic activity at a high level and have other favorable features such as a prolonged half-life in the blood circulation. The SOD derivatives having 2 copolymer molecules coupled with each SOD are particularly preferred.

The starting material SOD is the product obtained by extraction from its sources, namely living organisms such as animals (human, bovine, etc.), plants and microorganisms, by a known method or obtained by using genetic engineering techniques. The chemical structure (with respect to coordinating metal, molecular weight, amino acid sequence, etc.) of SOD has been elucidated to a considerable extent. SOD is now classified into three groups, namely F-SOD, Mn-SOD and Cu.Zn-SOD and has a molecular weight of 30,000 to 80,000 which depends on species and their subcellular compartment. The amino acid sequences of the three SODs also differ with each other. For details, reference may be made to Yoshihiko Oyanagi: "Superoxide and Medicine", pages 74-90, published by Kyoritsu Shuppan on May 25, 1981; Journal of Biological Chemistry, 246, 2875-2880 (1971); ibid., 250, 6107-6112 (1975); Proceedings of the National Academy of Sciences, 70, 3725-3729 (1973); and Archives of Biochemistry and Biophysics, 179, 243-256 (1977), among others. Most preferred SOD as the starting material is human-type Cu.Zn-SOD. This has a molecular weight of 33,000 and contains 22 or 24 amino groups in its molecule. Human-type SOD can be obtained, for example, by subjecting the human blood to heat treatment, ion exchange and gel filtration in that order or by using genetic engineering techniques.

The starting material copolymer can be produced by partial hydrolysis of a copolymer of a monomer corresponding to the above-mentioned constituent unit (a) and maleic anhydride [said partial hydrolysis being carried out to an extent such that a small number (on an average 0.5-2 per molecule) of maleic anhydride rings are remaining while other maleic anhydride rings have been hydrolyzed] or by partial half esterification of such copolymer with an alcohol [said partial half esterification being carried out to an extent such that a small number (on an average 0.5-2 per molecule) of maleic anhydride rings are remaining while other maleic anhydride rings have been half-esterified]. As examples of the copolymer obtainable by the above method, there may be mentioned a partially hydrolyzed styrene-, p-chlorostyrene-, p-bromostyrene- or α-methylstyrenemaleic anhydride copolymer; a partially half-esterified styrene-, p-chlorostyrene- p-bromostyrene- or α-methylstyrene-maleic anhydride copolymer (methyl ester, ethyl ester, propyl ester, n-butyl ester, methoxyethyl ester, ethoxyethyl ester, propoxyethyl ester, 2-butoxyethyl ester, 1,3-dimethoxy-2-propyl ester, 2,3-dimethoxy-1-propyl ester, 1,3-diethoxy-2-propyl ester, 2-ethoxy-3-methoxy-1-propyl ester, 1,3-dipropoxy-2-propyl ester, 1,3-dibutoxy-2-propyl ester, etc.); a partially hydrolyzed ethylene-, propylene-, α-butylene-, isobutylene-, 1-pentene-, 2-methyl-1-butene-, 1-hexene- or 1-heptene-maleic anhydride copolymer; a partially half-esterified ethylene-, propylene-, α-butylene-, isobutylene-, 1-pentene-, 2-methyl-1-butene-, 1-hexene- or 1-heptene-maleic anhydride copolymer (same esters as above being given as examples); a partially hydrolyzed vinyl acetate-maleic anhydride copolymer; a partially half-esterified vinyl acetate-maleic anhydride copolymer; a partially hydrolyzed methyl (meth)acrylatemaleic anhydride copolymer; a partially half-esterified methyl (meth)acrylate-maleic anhydride copolymer; a partially hydrolyzed ethyl (meth)acrylate-maleic anhydride copolymer; a partially half-esterified ethyl (meth)acrylate-maleic anhydride copolymer; and so on.

These copolymers all have both a hydrophobic group and a hydrophilic group and, as a result, have an adequate hydrophobicity and, at the same time, have polar carboxyl groups. Therefore, the SOD derivatives containing such copolymers therein can be reversibly bound to serum proteins and biomembranes and this results in extension of the half-life in the blood circulation as well as in improved transfer to organs. Among others, those SOD derivatives which have a styrene-derived group as the constituent unit (a) and those SOD derivatives which have a half-esterified group as the constituent unit (b) are preferable in producing these effects since they are relatively higher in hydrophobicity.

It is preferable that the mole ratio of the constituent unit (a) to the constituent units (b) and (c), i.e. $[(a)/\{(b)+(c)\}]$, in the copolymer be substantially within the range of about 1 to about 1.3. Said ratio is generally equal to 1. Those copolymers in which the mole ratio is less than 1 can hardly be obtained by copolymerization of a monomer corresponding to the constituent unit (a) and maleic anhydride. Those copolymers in which the ratio is more than 1.3, when the constituent unit (b) is a half-esterified one, are undesirable since their solubility in aqueous salt solutions is not so good as to allow their reaction with SOD in such aqueous solutions.

All the above-mentioned copolymers are known in the art. Their weight-average molecular weight is generally within the range of 800 to 20,000. From the viewpoint of transfer of the SOD derivatives obtained from these copolymers to affected sites, it is preferable that the copolymers have a weight-average molecular weight of not more than 3,000. No particular restrictions are placed on the molecular weight distribution of the copolymers. Thus, copolymers obtained by radical copolymerization of a monomer corresponding to the above-mentioned constituent unit (a) and maleic anhydride (copolymers with a weight-average molecular weight/number-average molecular weight ratio of about 2.0 or more) may be used as the raw materials after partial hydrolysis or partial half esterification without fractionation or may be subjected to fractionation to give products with a narrow molecular weight distribution followed by partial hydrolysis or partial half esterification for their use as the raw materials.

The following test examples illustrate the pharmacological characteristics of the SOD derivatives according to the invention.

Test Example 1

Figure 13:
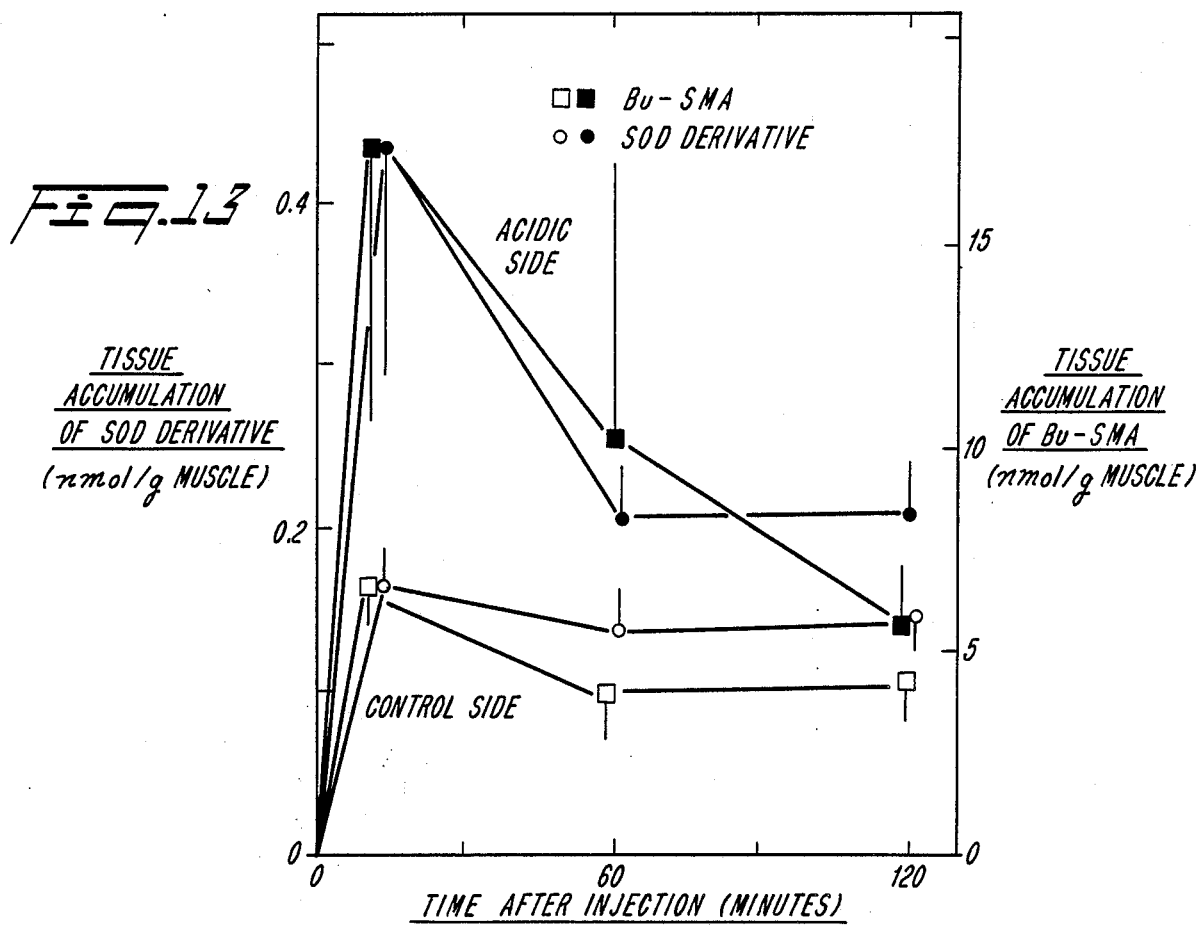
FIG. 13 shows the time course of the femoral tissue accumulation of the SOD derivative and Bu-SMA as intravenously administered to mice previously treated by intramuscular administration of 0.2 ml of HEPES buffer (pH 6.0) into the left femoral muscle (acidic side) and 0.2 ml of physiological saline into the right femoral muscle (control side)

Specific accumulation of the SOD derivative in the tissue with depressed local pH Using mice weighing about 20 g, 0.2 ml of 0.15 M-HEPES buffer (pH 6.0) and 0.2 ml of physiological saline were intramuscularly injected into the left and right femoral muscles, respectively. Immediately then, the $^{125}$I-labeled SOD derivative (14 nmol) prepared by the procedure described in Synthesis Example 2 or the $^3$H-labeled Bu-SMA (0.22 μmol) corresponding to the Bu-SMA used in Synthesis Example 2 was intravenously administered and the levels of radioactivity accumulated in the right and left femoral muscles were determined at the indicated intervals. The results are shown in FIG. 13. The radioactivity in the left femeral muscle (acidic side) is significantly higher than that in the right femoral muscle (control side), indicating that by virtue of the coupling of SOD to Bu-SMA, the SOD derivative according to Synthesis Example 2 is selectively taken up into acidic tissues (the pH at the site of inflammation is lowered).

Test Example 2

Ischemic damage inhibitory effect and anti-inflammatory effect

Method

Male SD rats (body weight: about 200 g) were starved for overnight and put in stress cages in groups of 6 animals each. The cases were immersed in water at 22° C. to the level of xiphoid of the animals for stress loading. It is known that this type of stress loading decreases the blood flow in the gastric mucosa of the rat and induces a local ischemia which triggers an acute inflammation leading to ulceration. After 2, 4 and 6 hours of stress loading, the cases were taken out from the water and the rats were sacrificed. Then, the stomach was excised. The isolated stomach was infused with 10% formalin for fixation. After this fixation, the lengths of linear ulcers were totaled and the sum was expressed as the ulcer index.

The test compound was administered immediately before restraint water-immersion. Rats in the control group received 0.5 ml of physiological saline, while rats in the test groups received 0.5 ml of a saline solution of SOD or the SOD derivative prepared in Synthesis Example 2 (1 mg/rat), all by the intravenous route.

Results

Figure 14:
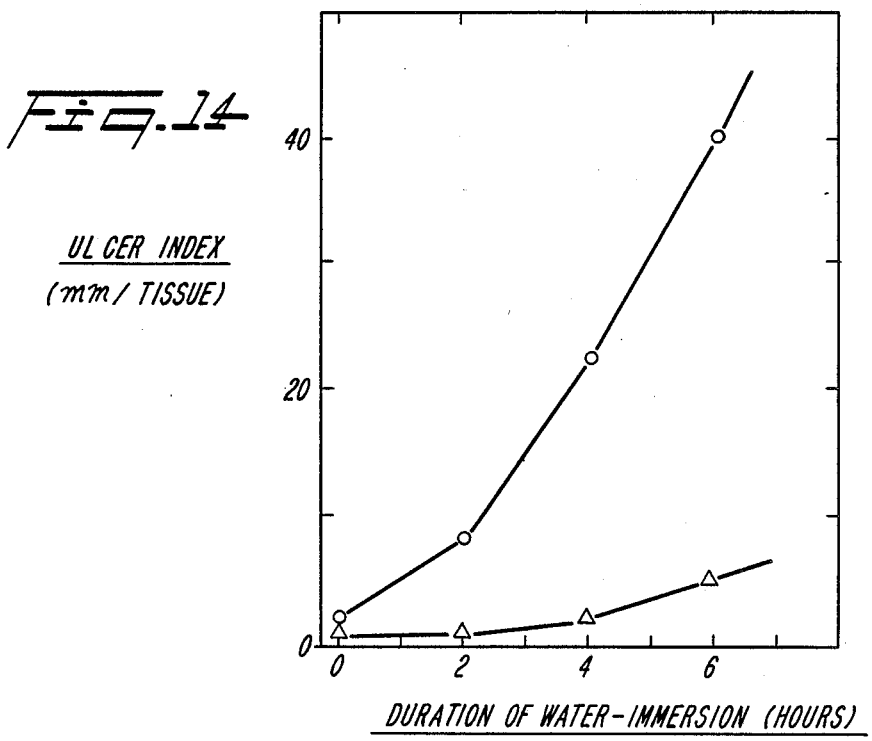
FIG. 14 shows the relationship between the ulcer index (mm/tissue) and the duration of water-immersion as found in a test of the SOD derivative for its antiulcer activity against acute gastric mucosal lesion induced in rats by restraint water-immersion.

FIG. 14 shows the ulcer index (mm/tissue) plotted against duration of water-immersion. In FIG. 14, the open circles represent the data for the control group and the triangles represent the data for the SOD derivative group. Incidentally, the result for the SOD group was omitted because it was substantially identical with the result of the control group.

It is clear from FIG. 14 that whereas the SOD group showed no sign of anti-ulcer effect, an overt inhibition of ulceration was noted in the SOD derivative group.

It is, thus, clear that the SOD derivative is an excellent ischemic damage preventing- anti-inflammatory agent for diseases accompanied by a depression of local tissue pH.

Test Example 3

Cerebral edema-preventing effect

Treatment of the right cerebral hemisphere of the rat (body weights: about 200 g) with liquid nitrogen for 30 seconds caused a marked unilateral cerebral edema. When the same rat was intravenously dosed with 0.2 μmol of the same $^3$H-labeled Bu-SMA as used in Test Example 1, the radioactivity was specifically accumulated on the injured side whose local pH was decreased [FIG. 15(2)]. When the same edematous rat was intravenously dosed with 27 nmol of the same $^{125}$I-labeled SOD derivative as used in Test Example 1, the radioactivity was specifically accumulated on the injured side [FIG. 15 (1)]. It is, therefore, apparent that the SOD derivative coupled to Bu-SMA according to Synthesis Example 2 is accumulated well in the injured brain tissue. This accumulation of the SOD derivative caused a marked reduction in edema.

Test Example 4

Oxygen poisoning-preventing effect

The intraperitoneal administration of 200 mg/kg of paraquat to mice (body wights: about 20 g) induces the formation of superoxide anion radical ($O_2^-$) which causes a liver cell injury which, in turn, causes a marked elevation of plasma GOT. The intravenous administration of 20 mg/kg of the same SOD derivative as above to such paraquat-treated mice caused a marked inhibition of elevation of plasma GOT level (FIG. 16). Unmodified SOD had no such protective effect, and hence the plasma GOT level was not different from that in the control group.

Furthermore, toxicological studies have shown the low toxicity of the SOD derivative.

As is clear from the foregoing results, the SOD derivative is effective for a variety of diseases associated with the superoxide anion radical and can be used as an anti-inflammatory agent, ischemic damage antagonist, cerebral anti-edemic agent, anti-paraquat intoxication agent, etc. and as a prophylactic agent for peptic ulcer and other gastrointestinal diseases due to the inflammation of the gastrointestinal mucosa.

The SOD derivatives of the present invention are of value as therapeutic drugs for ischemic heart diseases or as drugs for alleviating the side effects, which are associated with the superoxide anion radical, as caused by anti-cancer agents.

The dosage of the SOD derivative varies with the kind of disease, severity of the disease, patient's tolerance, and other factors. However, the usual daily dosage for adult humans is 0.1 to 500 mg and preferably 0.5 to 100 mg, either in a single dose or in a few divided doses. The SOD derivative may be provided in various dosage forms suitable for the respective routes of administration.

Thus, the SOD derivative can be formulated and prepared by the established pharmaceutical procedures. Therefore, the present invention covers a variety of pharmaceutical compositions containing at least one species of the SOD derivative as an active ingredient. Such pharmaceutical compositions can be manufactured sing pharmaceutically acceptable carriers, vehicles and other auxiliary substances which are commonly used in pharmaceutical practice.

When such pharmaceutical compositions are intended for oral administration, they are preferably provided in dosage forms suited to absorption from the gastro-intestinal tract. Tablets and capsules which are unit dosage forms for oral administration may contain binders such as syrup, gum arabic, gelatin, sorbitol, gum tragacanth, polyvinylpyrrolidone, etc., excipients such as lactose, corn starch, calcium phosphate, sorbitol, glycine, etc., lubricants such as magnesium stearate, talc, polyethylene glycol, silica, etc., disintegrators such as potato starch, etc., pharmaceutically acceptable wetting agents such as sodium laurylsulfate and so on. The tablets may be coated in the well-known manner. Liquid preparations for oral administration may be aqueous or oily suspensions, solutions, syrups, elixirs and so on, or may be lyophilisates which are extemporaneously reconstituted with water or other suitable vehicles Such liquid preparations may contain the usual additives inclusive of suspending agents such as sorbitol syrup, methylcellulose, glucose/sucrose syrup, gelatin, hydroxyethylcellulose, carboxymethylcellulose, aluminum stearate gel, hydrogenated edible oils and fats, etc.; emulsifiers such as lecithin, sorbitan monooleate, gum arabic, etc.; non-aqueous vehicles such as almond oil, fractionated coconut oil, oleaginous esters, propylene glycol, ethyl alcohol, etc.; preservatives such as methyl p-hydroxybenzoate, propyl p-hydroxybenzoate, sorbic acid, etc.; and so forth.

For preparing injections, the SOD derivative is dissolved in an appropriate solvent such as physiological saline, glucose solution for injection, etc. and the SOD derivative concentration is adjusted to 2 to 20 mg per 2 to 10 ml of solvent in the conventional manner to give injections for subcutaneous, intramuscular or intravenous administration. In preparing the above injections, pH-adjusting agents, buffers, stabilizers, preservatives, solubilizers and so forth may be added to the aqueous solution, if necessary.

The above-mentioned pharmaceutical composition can contain the SOD derivative in a concentration selected according to the form thereof and other factors generally in a concentration of about 0.01 to 50 percent by weight, preferably about 0.1 to 20 percent by weight.

The following examples are further illustrative of the present invention but are by no means limitative of the invention.

Reference Example 1

Synthesis of styrene-maleic anhydride copolymer

Maleic anhydride (383 g, 3.9 moles) was added to 3.7 liters of cumene and the mixture was stirred under reflux. To this solution was added dropwise over about 40 minutes a solution of 16.3 g (60 millimoles) of dicumyl peroxide and 203 g (1.95 moles) of styrene in 1.7 liters of cumene. After completion of the dropping, heating and stirring were continued for 1 hour. The reaction mixture thus obtained was allowed to stand overnight, the supernate was then removed and the viscous product adhering to the reaction vessel was recovered by dissolving the same in acetone. The acetone was distilled off from the thus recovered solution under reduced pressure tO give 353 g of a styrene-maleic anhydride copolymer (hereinafter referred to as SMA for short).

Fractionation of SMA

A 120.0-g portion of the SMA obtained in the above manner was dissolved in 3 liters of acetone. To this solution was added dropwise 4.9 liters of n-hexane with stirring over about 1 hour. The resultant opaque acetone-n-hexane mixture was transferred to another vessel and, to this mixture, 9.74 liters of n-hexane was added dropwise with stirring over about 1.5 hours. The viscous matter adhering to the vessel wall was recovered by dissolving the same in acetone. From the solution thus recovered, the acetone was distilled off under reduced pressure. The residue was dried overnight under vacuum at temperatures of 70°–80° C. Thus was obtained 49.2 g of a fractionated precipitate of SMA.

A 40.0-g portion of the thus obtained fraction of SMA was dissolved in 1 liter of acetone. To the solution were added 3.8 kg of glass beads (average grain size: 0.1 mm) silane-treated on the surface and acetone was evaporated to give glass beads bearing SMA on the surface thereof.

A column, 80 mm in inside diameter and 80 cm in length, was packed with the above SMA-bearing glass beads together with 1.4 liters of a mixture of acetone and n-hexane (volume ratio at 25° C.: 24:76) and, while maintaining the column system temperature at 25° C., two acetone-n-hexane mixtures differing in volume ratio, namely (i) 1.6 liters of an acetone-n-hexane mixture with a volume ratio at 25° C. of 24:76 and (ii) 6.0 liters of an acetone-n-hexane mixture with a volume ratio at 25° C. of 37:63, were supplied dropwise to the column system from the top thereof in that order, followed by further dropwise supply of 3.0 liters of acetone. Eluted fractions corresponding to the abovementioned 37:63 (by volume) acetone-n-hexane mixture were collected and low-boiling fractions were distilled off under reduced pressure. The residue was dried overnight under vacuum at temperatures of 70°–80° C. Thus was obtained the desired SMA fraction in a yield of 31.8 g. The weight-average molecular weight ($\overline{Mw}$) and number-average molecular weight ($\overline{Mn}$) of this fractionated SMA were determined by gel permeation chromatography (hereinafter referred to as GPC for short; tetrahydrofuran eluent, polystyrene standard) to be $\overline{Mw}$ 1,340 and $\overline{Mn}$ 1,220 ($\overline{Mw}/\overline{Mn}$=1.10). The $\overline{Mn}$ as determined by using a vapor pressure osmometer was 1,210. The maleic anhydride content in the fractionated SMA obtained as determined by potentiometric titration was 47.3 mole percent.

Partial half butyl esterification of the fractionated SMA

An about 40-ml ampul equipped with a magnetic stirrer was charged with 10.0 g of the above fractionated SMA, 2.20 g of n-butyl alcohol, 0.10 g of anhydrous lithium acetate and 20 ml of dioxane and then sealed. The contents of this ampul were heated at 90° C. with stirring for 20 hours. A small quantity of the reaction mixture was taken and analyzed for unreacted n-butyl alcohol by gas chromatography using ethylcellosolve as an internal standard, and the degree of half butyl esterification of the maleic anhydride ring in the copolymer was calculated based on the conversion of the n-butyl alcohol charged and was found to be 62%. Then, the reaction mixture was diluted with 20 ml of dioxane, and the dilute solution was added dropwise to 400 ml of n-hexane for reprecipitation. The precipitate was recovered and dried overnight under vacuum at about 60° C. to give 11.5 g of the desired partially half butylesterified styrene-maleic anhydride copolymer (Bu-SMA). The residual maleic anhydride ring content in this copolymer was determined on the basis of the absorption intensities at the wave numbers 1780 cm$^{-1}$ and 700 cm$^{-1}$ as found by infrared spectrometry (FT-IR, KBr disk method) and was found to be 30.3 mole percent (the number of maleic anhydride rings per molecule of Bu-SMA was, on the average, 1.8). The $\overline{Mw}$ and $\overline{Mn}$ determined by GPC were 1,530 and 1,440, respectively ($\overline{Mw}/\overline{Mn}$=1.06).

Synthesis Example 1

In 10 ml of 0.1 M aqueous sodium hydrogen carbonate (pH 8.0), 50 mg ($1.5 \times 10^{-6}$ moles) of human erythrocyte SOD (3,000 units/mg) were dissolved with stirring at 37° C. To the solution was added portionwise 80 mg (5 mM; this concentration being the final Bu-SMA concentration in the reaction mixture; hereinafter the same shall apply) of a partially half butyl-esterified styrene-maleic anhydride copolymer [$\overline{Mw}$=1,600; degree of esterification=60 mole percent; maleic anhydride ring content=25 mole percent (the number of maleic anhydride rings per molecule being, on the average, 1.6)] obtained by partial half butyl esterification of a styrene-maleic anhydride copolymer [product of radical polymerization using dicumyl peroxide as the initiator; styrene-maleic anhydride mole ratio in the product=1:1 ; $\overline{Mw}$=1,280; molecular weight distribution: $\overline{Mw}/\overline{Mn}$ =not more than 1.20] as a solid powder, and the reaction was allowed to proceed for 1 hour.

Figure 2:
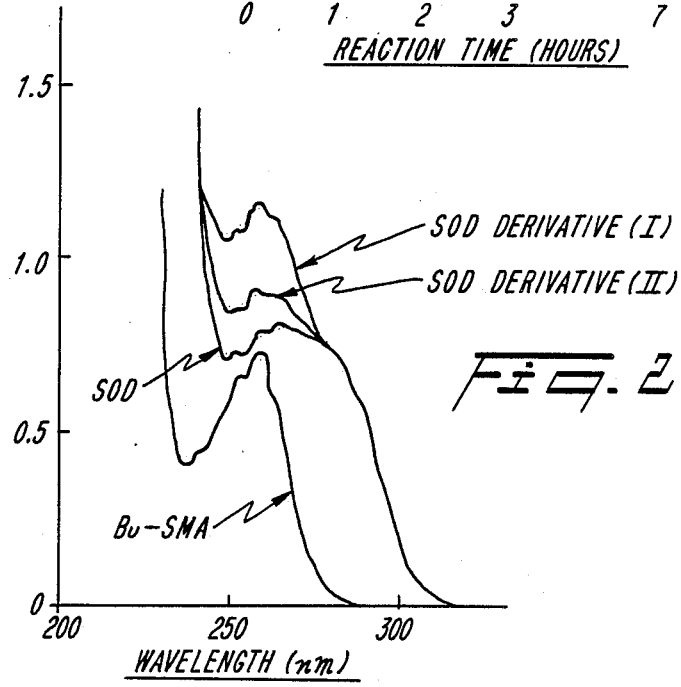
FIG. 2 shows UV spectra of the SOD derivatives obtained in Synthesis Example 1 and Synthesis Example 2 respectively and the starting material SOD.
Figure 8:
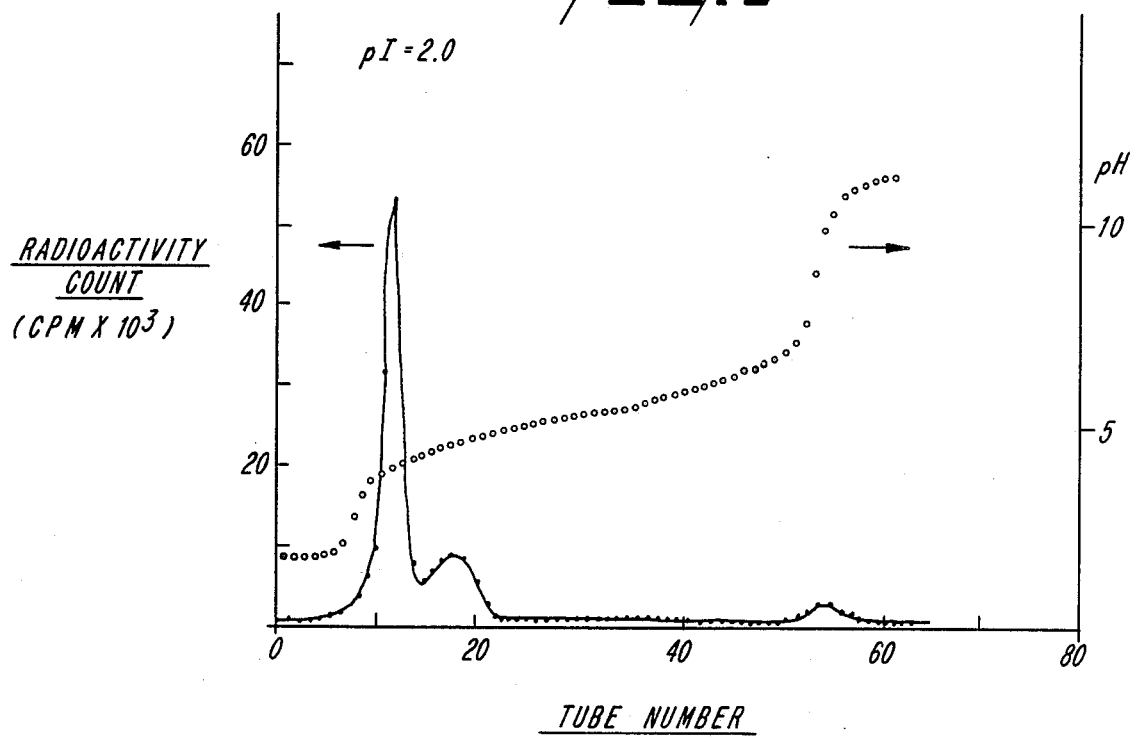
FIG. 8 shows the results, given in terms of pH and radioactivity, of isoelectric focusing of the SOD derivative obtained in Synthesis Example 1 after labeling with $^{51}Cr$.

To follow the course of the reaction of the amino group of human erythrocyte SOD with Bu-SMA, the residual amino group content was determined using sodium trinitrobenzenesulfonate (TNBS). The species of human erythrocyte SOD as used in this example contains 22 amino groups per molecule and about 10 to 11 of the amino groups can be assayed by the TNBS method. It was confirmed that 20 mole percent of the amino groups (corresponding to about 44 mole percent of titratable amino groups) of the human erythrocyte SOD had reacted with Bu-SMA under the above reaction conditions. The reaction mixture was filtered and the filtrate was subjected to gel filtration by injecting it into a K50/30 column (trademark; Pharmacia Fine Chemicals) packed with Sephadex G-100 (trademark; Pharmacia Fine Chemicals). A mixed solution of 20 mM ammonium hydrogen carbonate and ammonium carbonate was used as the eluent. Eluted fractions were measured at 280 nm and the fractions showing absorption were collected, concentrated by means of an ultrafiltration membrane (Sartorius SM 145-39) and lyophilized to give 52 mg of a white powder. The UV absorption spectrum of the powder obtained [SOD derivative (I) in FIG. 2] and the UV absorption spectra of the starting materials SOD and Bu-SMA were measured at pH 7.4 using phosphate buffer. The spectra are shown in FIG. 2. A 5-µl portion of a $^{51}$Cr-labeled sample (reaction product) prepared in the same manner was subjected to isoelectric focusing on Ampholine (pH 1.5–6.0; 700 mV; 12 hours of electrification; fractionation: 1 ml/fraction), followed by pH and radioactivity measurements. The results thus obtained are shown in FIG. 8. The powder obtained had an isoelectric point of 2.0. The protein content in the white powder obtained as measured by the Lowry method was 80%. Based on these results, the number of Bu-SMA molecules per SOD molecule was determined.

On the basis of the above data, the white powder obtained was identified as the SOD derivative containing, on an average, 5 molecules of Bu-SMA (mole ratio between

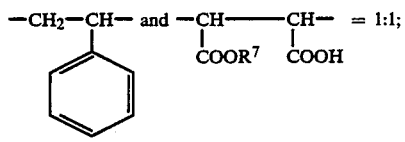

$-CH_2-CH-$ and $-CH-CH-$ = 1:1;
           |              |       |
          (phenyl)       COOR$^7$ COOH degree of butyl esterification=60%; $\overline{Mw}$=1,600) bound to each SOD molecule (by reaction of amino groups of SOD with a maleic anhydride ring of Bu-SMA).

Synthesis Example 2

Figure 9:
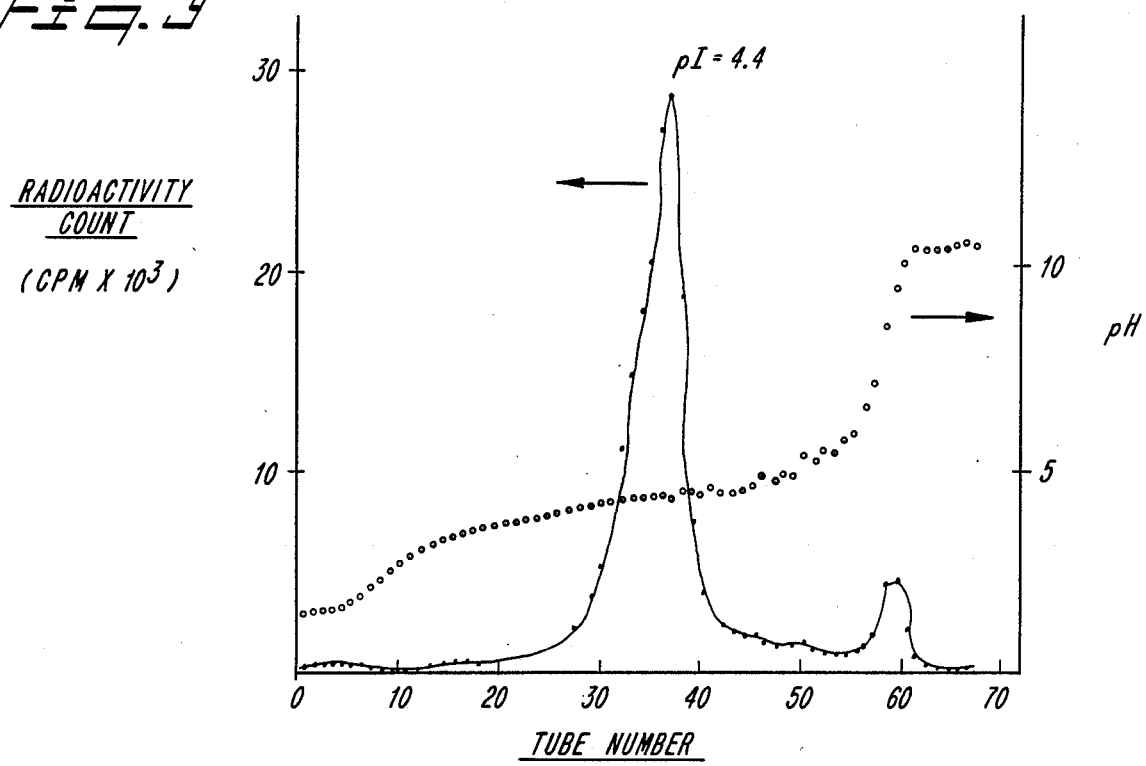
FIG. 9 shows the results, given in terms of pH and radioactivity, of isoelectric focusing of the SOD derivative obtained in Synthesis Example 2 after labeling with $^{51}Cr$.

In 10 ml of 0.1M aqueous sodium hydrogen carbonate (pH 8.0) was dissolved 50 mg of human erythrocyte SOD (3,000 units/mg) at 37° C. with stirring. To the solution was added portionwise 30 mg (1.9 mM) of the same Bu-SMA as used in Synthesis Example 1, and the Bu-SMA was reacted with the above human erythrocyte SOD in the same manner as in Synthesis Example 1. The reaction mixture was then treated in the same manner as in Synthesis Example 1 to give 45 mg of a white powder. The UV absorption spectrum of the above white powder as measured in the same manner as in Synthesis Example 1 is shown in FIG. 2 [SOD derivative (II)]. The results of pH and radioactivity measurements following isoelectric focusing are shown in FIG. 9. The powder obtained showed an isoelectric point of 4.4. The results of assaying of the residual amino group content by the TNBS method confirmed that about 9 mole percent of the amino groups in the starting material SOD (corresponding to about 20 mole percent of titratable amino groups) had reacted with Bu-SMA.

On the basis of the above data, the white powder obtained was identified as an SOD derivative with, on an average, 2 molecules of Bu-SMA being bound to each SOD molecule.

Synthesis Example 3

In 1 ml of 0.1 M aqueous sodium hydrogen carbonate (pH 8.0) was dissolved 5 mg ($1.5 \times 10^{-7}$ moles) of human erythrocyte SOD (3,000 units/mg). To the solution was added 4 mg (2.5 mM) of the same Bu-SMA as used in Synthesis Example 1, and the reaction was allowed to proceed in the same manner at 37° C. The relationship between the amino group content in SOD and the reaction time is shown in FIG. 1. The amino group assaying was performed by the TNBS method. The human erythrocyte SOD used contains 22 amino groups per molecule and about 10-11 of them are assayable by the TNBS method. It was confirmed that, under the above reaction conditions, about 38 mole percent of the titratable amino groups had reacted with Bu-SMA in 1 hour. The SOD derivative with about 4 molecules of Bu-SMA being bound to each SOD molecule could be obtained. After 2 hours of reaction, the same quantity of Bu-SMA was further added to the reaction mixture. In this case, the amino group content further decreased, as shown in FIG. 1 (--●--). This clearly indicates that the quantity of Bu-SMA bound to the SOD molecule can be controlled by varying the quantity of Bu-SMA added to the reaction.

Synthesis Example 4

In 1 ml of 0.1M aqueous sodium hydrogen carbonate (pH 8.0) was dissolved 10 mg ($3.0 \times 10^{-7}$ moles) of human erythrocyte SOD (3,000 units/mg). To the solution was added one of the partially hydrolyzed or partially half-esterified styrene-maleic anhydride copolymers given in Table 1 to a final concentration (in the reaction mixture) of 2.5 mM. The reaction was carried out at 37° C. for 1 hour. Thereafter, the residual amino group content in SOD was determined by the TNBS method. In each case, it was confirmed that the loss of amino groups amounted to 15–25 mole percent of titratable amino groups. In each case, the SOD derivative with, on an average, 1.7–2.8 molecules of styrene-maleic anhydride copolymer being bound to each SOD molecule was obtained.

TABLE 1

| No. | Esterification (Yes or No) and Kind | Degree of esterification (mole percent) | Maleic anhydride ring content (rings/molecule) | $\overline{Mw}$ |
|---|---|---|---|---|
| 4-1 | Yes (butyl ester) | 60 | 1.3 | 1200 |
| 4-2 | Yes (butyl ester) | 40 | 2.0 | 1600 |
| 4-3 | Yes (butyl ester) | 70 | 1.5 | 1600 |
| 4-4 | Yes (butyl ester) | 60 | 1.9 | 2000 |
| 4-5 | Yes (methyl ester) | 60 | 1.3 | 1600 |
| 4-6 | Yes (ethyl ester) | 60 | 1.7 | 1600 |
| 4-7 | Yes (methoxyethyl ester) | 60 | 1.3 | 1600 |
| 4-8 | Yes (2-butoxyethyl ester) | 60 | 1.7 | 1600 |
| 4-9 | Yes (1,3-dimethoxy-2-propyl ester) | 60 | 1.4 | 1600 |
| 4-10 | Yes (1,3-dibutoxy-2-propyl ester) | 60 | 1.3 | 1600 |
| 4-11 | No | — | 2.3 | 1400 |

Synthesis Example 5

The reaction and isolation procedures of Synthesis Example 4 were carried out in the same manner except that a partially hydrolyzed isobutene-maleic anhydride copolymer ($\overline{Mw}$=2,500; maleic anhydride ring content =3.0 rings/molecule) was used in lieu of the styrene-maleic anhydride copolymer used in Synthesis Example 4. The SOD derivative with about 4 molecules of isobutene-maleic anhydride copolymer being bound to each SOD molecule was obtained.

Synthesis Example 6

The reaction and isolation procedures of Synthesis Example 4 were carried out in the same manner except that one of the copolymers given in Table 2 was used in lieu of the styrene-maleic anhydride copolymer used in Synthesis Example 4. Thus, the corresponding SOD derivatives were obtained.

TABLE 2

| No. | Kind of Copolymer | Esterification (Yes or No) and Kind | Degree of esterification (mole percent) | $\overline{Mw}$ |
|---|---|---|---|---|
| 6-1 | p-Chlorostyrene-maleic anhydride copolymer | Yes (butyl ester) | 60 | 1800 |
| 6-2 | p-Bromostyrene-maleic anhydride copolymer | Yes (butyl ester) | 60 | 1900 |
| 6-3 | α-Methylstyrene-maleic anhydride copolymer | Yes (butyl ester) | 60 | 1800 |
| 6-4 | Ethylene-maleic anhydride copolymer | No | — | 2500 |
| 6-5 | Ethylene-maleic anhydride copolymer | Yes (butyl ester) | 60 | 3000 |
| 6-6 | Propylene-maleic anhydride copolymer | No | — | 2000 |
| 6-7 | Propylene-maleic anhydride copolymer | Yes (butyl ester) | 60 | 2500 |
| 6-8 | Isobutylene-maleic anhydride copolymer | Yes (ethyl ester) | 60 | 2800 |
| 6-9 | Isobutylene-maleic anhydride copolymer | Yes (butyl ester) | 60 | 3000 |
| 6-10 | α-Butylene-maleic anhydride copolymer | Yes (butyl ester) | 60 | 2800 |
| 6-11 | 1-Pentene-maleic anhydride copolymer | Yes (butyl ester) | 60 | 2800 |
| 6-12 | 2-Methyl-1-butene-maleic anhydride copolymer | Yes (butyl ester) | 60 | 2500 |
| 6-13 | 1-Hexene-maleic anhydride copolymer | Yes (butyl ester) | 60 | 2500 |
| 6-14 | 1-Heptene-maleic anhydride copolymer | No | — | 2000 |
| 6-15 | 1-Heptene-maleic anhydride copolymer | Yes (butyl ester) | 60 | 2000 |
| 6-16 | Vinyl acetate-maleic anhydride copolymer | No | — | 2500 |
| 6-17 | Vinyl acetate-maleic anhydride copolymer | Yes (butyl ester) | 60 | 2500 |
| 6-18 | Methyl acrylate-maleic anhydride copolymer | Yes (butyl ester) | 60 | 2500 |
| 6-19 | Ethyl acrylate-maleic anhydride copolymer | Yes (butyl ester) | 60 | 2600 |
| 6-20 | Methyl methacrylate-maleic anhydride copolymer | Yes (butyl ester) | 60 | 2000 |
| 6-21 | Ethyl methacrylate-maleic anhydride copolymer | Yes (butyl ester) | 60 | 2200 |

(The maleic anhydride ring content in each copolymer was about 1.5 rings per molecule.)

Synthesis Example 7

A specified quantity (Table 3) of human erythrocyte SOD (manufactured by Sigma) was dissolved in 0.1M aqueous sodium hydrogen carbonate (pH 8.0) to a concentration of 5 mg/ml. To the solution was added a specified quantity of a partially hydrolyzed styrene-maleic anhydride copolymer (molecular weight=about 1,400; maleic anhydride ring content=about 1.0 ring/molecule), a partially hydrolyzed p-bromostyrenemaleic anhydride copolymer (molecular weight=about 1,600; maleic anhydride ring content=-about 1.5 rings/molecule), a partially hydrolyzed α-methylstyrene-maleic anhydride copolymer (molecular weight=about 1,600; maleic anhydride ring content=-about 3.3 rings/molecule) or a partially hydrolyzed isobutylenemaleic anhydride copolymer (molecular weight=2,500; maleic anhydride ring content=about 3.5 rings/molecule), and the reaction was allowed to proceed at 25° C. for 1 hour. The reaction mixture was then injected into a K26/40 column (trademark; Pharmacia Fine Chemicals) packed with Sephadex G-75 Superfine (trademark; Pharmacia Fine Chemicals) for gel filtration. A mixed solution of 10 mM ammonium hydrogen carbonate and ammonium carbonate was used as the eluent. Eluted fractions were measured at 280 nm and 254 nm, and the fractions showing absorption other than the unreacted copolymer fractions were collected and lyophilized to give the SOD derivative in a white powder form. The results thus obtained are shown in Table 3. The reacted amino groups in SOD were determined by the TNBS method. The human erythrocyte SOD species used contains 22 amino groups per molecule and about 10-11 of them are titratable by the TNBS method.

TABLE 3

| No. | SOD (mg) | Partially hydrolyzed copolymer (mg) | Approximate number of those amino groups in SOD that have reacted | Yield of SOD derivative (mg) |
|---|---|---|---|---|
| 7-1 | 19 | Styrene-maleic anhydride copolymer 15 | 3 | 15 |
| 7-2 | 19 | p-Bromostyrene-maleic anhydride copolymer 16 | 3 | 18 |
| 7-3 | 18 | α-Methylstyrene-maleic anhydride copolymer 11 | 3 | 17 |
| 7-4 | 17 | Isobutylene-maleic anhydride copolymer 9 | 2 | 10 |

The IR absorption spectra (FT-IR, KBr disk method) of human erythrocyte SOD and bovine erythrocyte SOD are shown in FIG. 4 (1) and FIG. 4 (2), respectively. The IR absorption spectra (FT-IR, KBr disk method) of the SOD derivatives No. 7-1, No. 7-2 and No. 7-3 given in Table 3 are shown in FIG. 5, FIG. 6 and FIG. 7, respectively.

Figure 5:
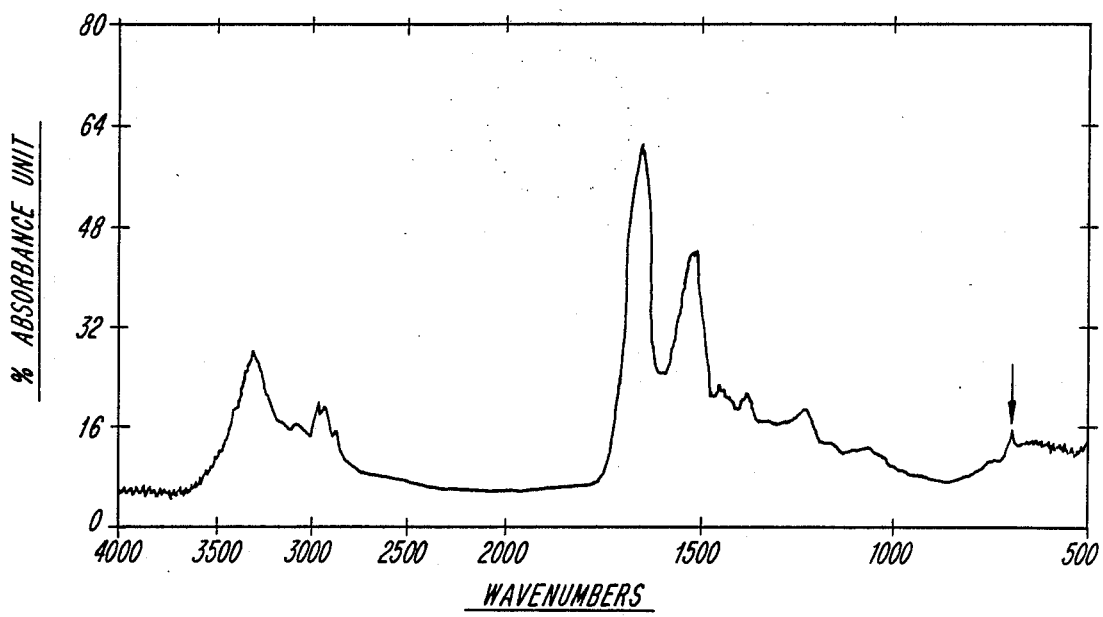
FIG. 5, FIG. 6 and FIG. 7 show IR spectra of the SOD derivatives obtained in Synthesis Examples No. 7-1, No. 7-2 and No. 7-3, respectively.
Figure 6:
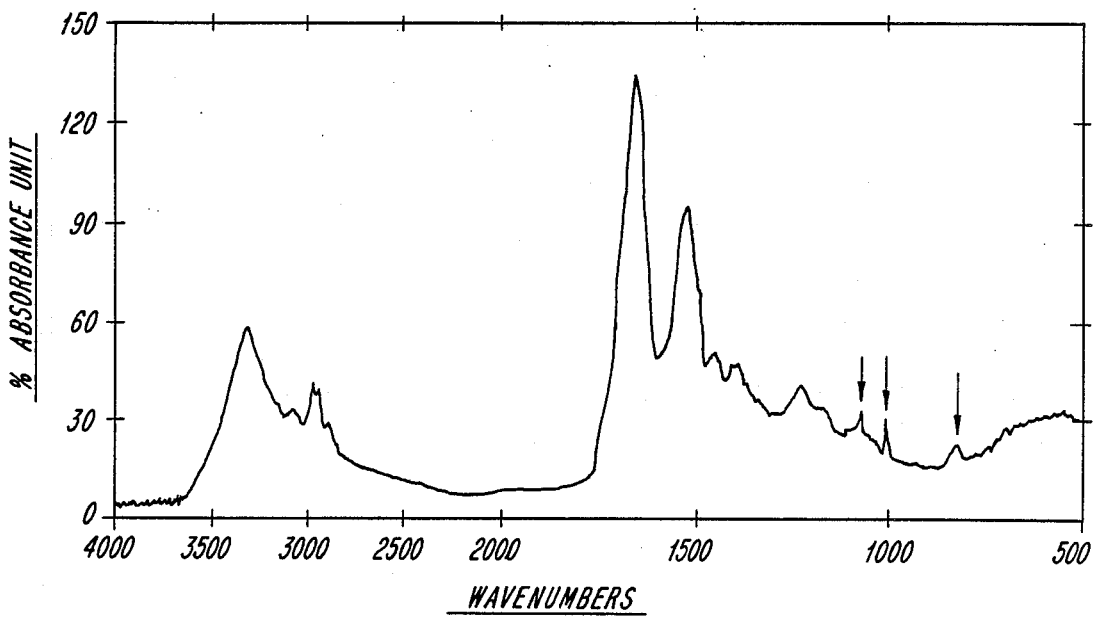
Figure 7:
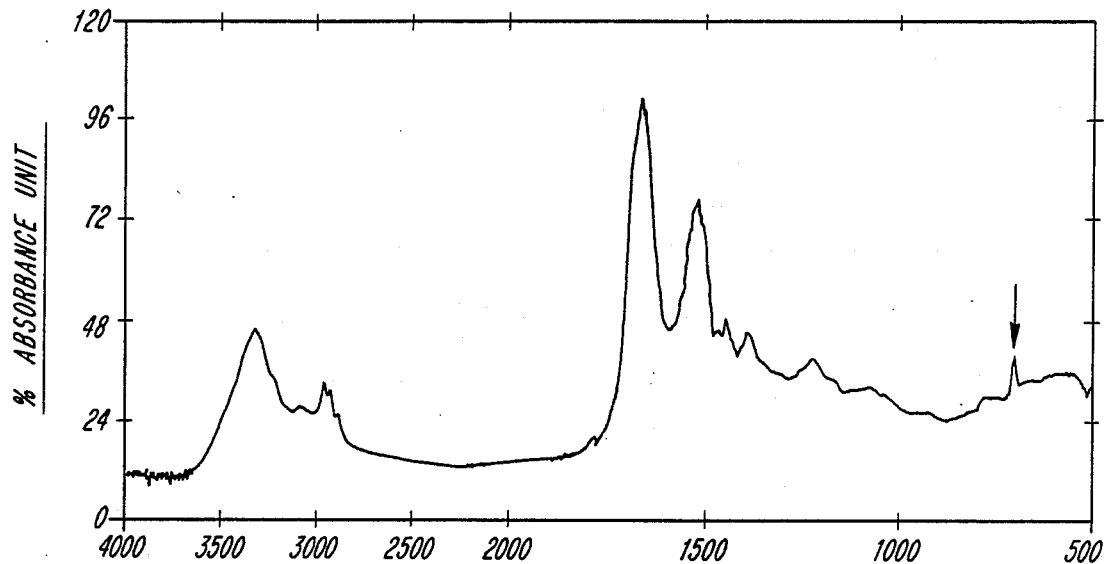

In each of FIGS. 5-7, an absorption or absorptions (each indicated by an arrow) due to the copolymer can be observed in addition to the absorption spectrum of human erythrocyte SOD. The absorption spectra shown in these figures thus indicate that each copolymer is bound to SOD.

The same reaction and isolation procedures as mentioned above were carried out using bovine erythrocyte SOD in lieu of human erythrocyte SOD to give the corresponding SOD derivatives each having an IR absorption spectrum similar to those shown in FIGS. 5-7.

Test Example 5

Figure 3:
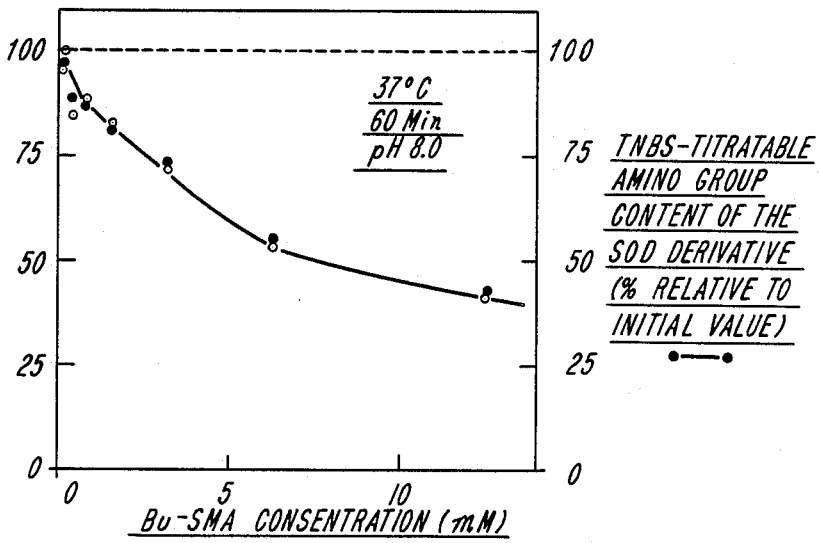
FIG. 3 shows the relationship between the Bu-SMA concentration in the reaction mixture obtained in Test Example 5 and the TNBS-titratable amino group content of the SOD derivative obtained and the relationship between said Bu-SMA concentration and the SOD activity of said SOD derivative.

Human erythrocyte SOD (5 mg/ml) was reacted with Bu-SMA, which was used in various concentrations (0.14, 0.37, 0.75, 1.5, 3, 6 and 12 mM), at 37° C. and pH 8.0 for 1 hour. In this way, various SOD derivatives differing in the quantity of Bu-SMA bound to SOD were prepared. The relationship between the bound Bu-SMA content in the SOD derivative and the enzymatic activity was studied. The enzymatic activity measurement was carried out by the method described in Journal of Biological Chemistry, 244, 6049–6055 (1965). The relationship between the Bu-SMA concentration in the reaction mixture and the residual amino group content in the SOD derivative obtained (as determined by the TNBS method) and the relationship between said Bu-SMA concentration and the enzymatic activity are shown in FIG. 3. The data shown in FIG. 3 indicate that when the Bu-SMA concentration is 6 mM, about 50% of the TNBS-titratable amino groups in the SOD derivative obtained remain intact (this means that since, as mentioned above, about 10–11 amino groups out of the 22 amino groups occurring in each molecule of the starting material SOD are reactive with TNBS, 5 amino groups participate in the reaction in this case, with the remaining 17 amino groups kept unreacted), with 50% of the original enzymatic activity being maintained and that when the quantity of bound Bu-SMA becomes greater, the enzymatic activity becomes lower than 50% of the original. Therefore, extreme chemical modification of SOD using the copolymer is not favorable to the maintenance of the enzymatic activity but it is necessary to restrict the number of copolymer molecules bound to each SOD molecule to about 6 or less. As shown in FIG. 3, the SOD derivative in which two Bu-SMA molecules are bound to each SOD molecule keeps 80% of the original enzymatic activity of SOD itself.

Figure 11:
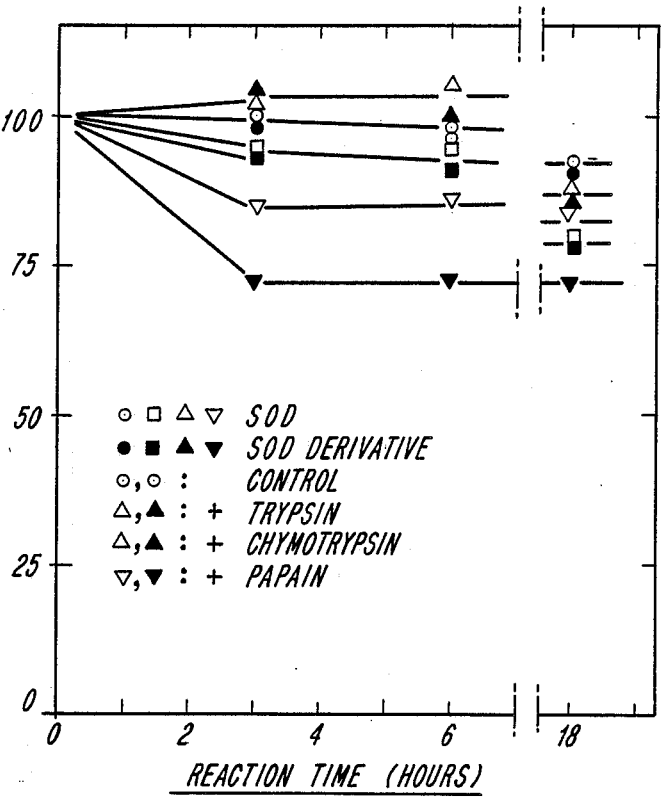
FIG. 11 comparatively shows the resistances to various protease species of the SOD derivative obtained in Synthesis Example 2 and the starting material SOD.

The SOD derivative obtained in Synthesis Example 2 and the starting material SOD were compared with respect to sensitivity to protease. The reaction was carried out at pH 7.4 and 37° C. The SOD derivative and SOD in a concentration of 15 units per milliliter (5 μg/ml) were each reacted with 0.1 mg/ml of trypsin, chymotrypsin or papain. The results thus obtained are shown in FIG. 11. Both lost their enzymaic activity slightly under the action of papain but were stable against other protease species without substantial inactivation. It was therefore concluded that modification of SOD with the copolymer did not change stability of the enzyme SOD.

Test Example 6

Figure 10:
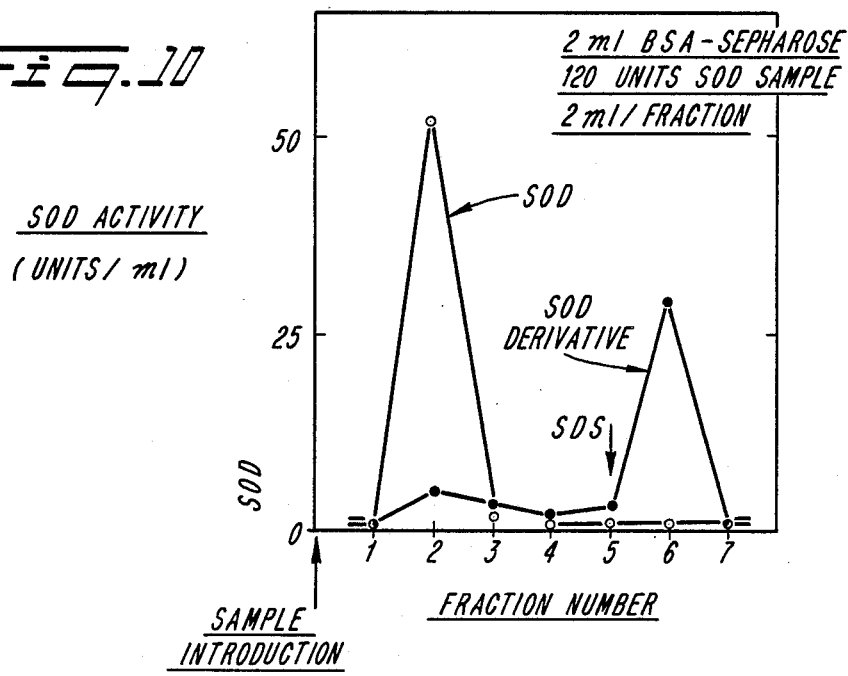
FIG. 10 shows the results of bovine serum albumin-Sepharose column affinity chromatography of the SOD derivative obtained in Synthesis Example 2 and the starting material SOD.

The SOD derivative obtained in Synthesis Example 2 and the starting material SOD were each subjected to bovine serum albumin-Sepharose column affinity chromatography. The results obtained are shown in FIG. 10. The starting SOD was not bound to albumin but wholly passed through the column. As for the SOD derivative, 95% or more was bound to the albumin column. Treatment of the column with 0.1% sodium dodecyl-sulfate (SDS) caused elution of a considerable portion of the SOD derivative but, under these conditions, about 30% of the SOD derivative still remained bound to the column. The subsequent denaturing treatment of the column with guanidine hydrochloride led to complete elution of the SOD derivative. When the SDS concentration was 0.5%, almost quantitative elution of the SOD derivative from the albumin column was attained by SDS treatment as well. These facts indicate that the SOD derivative with Bu-SMA bound to SOD, unlike the starting material SOD, has strong affinity to albumin.

Figure 12:
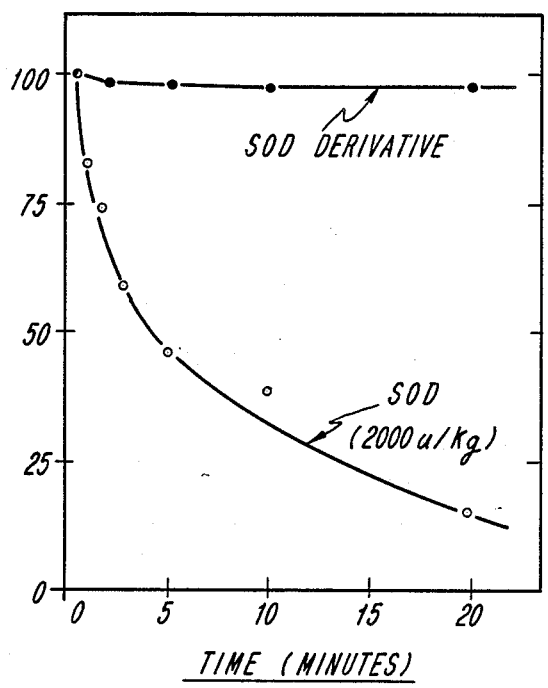
FIG. 12 shows the time course of the plasma concentration of the SOD derivative obtained in Synthesis Example 2 as intravenously administered to rats and that of the starting material SOD as intravenously administered to rats.

Then, the SOD derivative obtained in Synthesis Example 2 or the starting material SOD was intravenously administered to rats and the changes of the SOD derivative concentration and the SOD concentration in plasma were followed. The results obtained are shown in FIG. 12. As is clear from FIG. 12, the plasma concentration of the SOD derivative was maintained at a high level for a very long period (half-life=6 hours) while the plasma concentration of the starting material SOD decreased in a short period of time (half-life=5 minutes). This is supposedly due to strong binding of the SOD derivative to plasma albumin owing to the presence of Bu-SMA.

The SOD derivatives obtained in Synthesis Examples 4, 5 and 6 were also subjected to bovine serum albumin-Sepharose column affinity chromatography, which was carried out in the same manner as above. For each of the SOD derivatives, at least 90% was bound to the albumin column and elution therefrom required sodium dodecyl sulfate (SDS) treatment. This indicates that each SOD derivative is bound strongly to albumin. This binding is supposedly due to the presence of a hydrophobic group and the carboxyl group in the copolymer coupled with SOD.

The reaction and isolation procedures of Synthesis Example 2 were repeated in the same manner except that bovine erythrocyte SOD was used in lieu of the human erythrocyte SOD used in Synthesis Example 2. Thus, the SOD derivative in which two molecules of Bu-SMA were bound to each bovine erythrocyte SOD molecule was obtained. For this SOD derivative, too, the same results as the above-mentioned test results were obtained. Thus, no differences were observed between human erythrocyte SOD and bovine erythrocyte SOD.

Test Example 7

The SOD derivative obtained in Synthesis Example 2 was mixed with rat serum and the mixture was subjected to gel filtration (Sephacryl S-200; SD rat serum 0.2 ml; sample 0.2 mg). Elution of the SOD derivative in a serum protein-bound (mainly albumin-bound) form was observed. On the other hand, in gel filtration of a mixture of the starting material SOD and rat serum, which was carried out in the same manner as above, SOD did not interact with serum protein but was eluted in a fraction corresponding to its original molecular weight, namely about 33,000.

In a further test, the above SOD derivative was mixed with analbuminemic rat serum and the mixture was subjected to gel filtration in the same manner as above. A considerable portion of the SOD derivative was eluted in a form bound to serum protein in a nonalbumin fraction. Therefore, it is considered that when the plasma albumin concentration is low, the SOD derivative behaves in a form bound to other species of serum protein. This indicates that the SOD derivative can be effective against diseases in which a decreased serum albumin concentration is observed.

Test Example 8

The $^{51}$Cr-labeled SOD derivative prepared in accordance with Synthesis Example 2, the $^{3}$H-labeled Bu- SMA corresponding to the Bu-SMA used in Synthesis Example 2, and SOD were respectively administered to rats (body weights about 200 g) intravenously in the dose of 200,000 cpm/rat and the levels of radioactivity in various organs were determined after 1 hour. The results are shown in Table 4. It is apparent that the urinary excretion of the SOD derivative is markedly suppressed, the plasma half-life of the SOD derivative is prolonged, and the SOD derivative is distributed in high concentrations in the organs.

TABLE 4

Tissue distribution of radioactive SOD

| Organ | cpm/organ | | |
|---|---|---|---|
| | SOD | SOD derivative | Bu-SMA |
| Blood (cpm/ml) | 47 | 4400 | 7045 |
| Brain | 27 | 262 | 230 |
| Lung | 190 | 849 | 454 |
| Heart | 127 | 262 | 383 |
| Liver | 261 | 11667 | 832 |
| Kidney | 16200 | 33720 | 434 |
| Urine | 89725 | 67 | 248 |
| Spleen | 80 | 496 | 385 |
| Stomach | 120 | 271 | 363 |
| Small intestine (cpm/2 g) | 160 | 1300 | 159 |
| Muscle (50 g) | 3250 | 11778 | 11900 |

It is apparent from the above results of various test examples that the SOD derivative has enzymatic activity approximating that of SOD and shows a markedly prolonged plasma half-life as compared with SOD. Furthermore, as the SOD derivative undergoes reversible interaction with serum protein, this property is very instrumental in achieving the translocation of SOD to the affected organ or site. It is acknowledged that pH is lowered in the loci of inflammation and ischemic lesions and protonated carboxyl group-containing compounds are selectively accumulated in such regions. Since the SOD derivative contains carboxyl groups, it is expected that these carboxyl groups are protonated in vivo and, thereby, the SOD derivative is accumulated efficiently in the loci of inflammation and ischemic lesions. Thus, the SOD derivative displays excellent effects as a prophylactic and therapeutic agent for ulcers and other diseases associated with mucosal inflammation and for ischemic diseases.

Some examples of the dosage form which contains the SOD derivative obtained in Synthesis Example 2, a typical example of the SOD derivative according to the invention, as the active ingredient are shown below.

Dosage Form Example 1

Enteric coated capsules were prepared by a conventional method using the following ingredients:

SOD derivative obtained in Synthesis Example 2 20 mg

| | |
|---|---|
| SOD derivative obtained in Synthesis Example 2 | 20 mg |
| Lactose | 46 mg |
| Corn starch | 16 mg |
| Crystalline cellulose | 12 mg |
| Cellulose glycolate | 5 mg |
| Sorbitol | 10 mg |
| Total (per capsule) | 109 mg |

The above capsules are administered to adult humans generally at a dosage of 2 capsules three times a day after each meal.

Dosage Form Example 2

Enteric coated tablets are prepared by a conventional method using the following ingredients:

| | |
|---|---|
| SOD derivative obtained in Synthesis Example 2 | 20 mg |
| Lactose | 79 mg |
| Corn starch | 45.5 mg |
| Magnesium stearate | 0.5 mg |
| Total (per tablet) | 145 mg |

The above tablets are administered to adult humans generally at a dosage of 2 tablets three times a day after each meal.

Dosage Form Example 3

A preparation for injection was prepared in the following manner: A 10-mg portion of the SOD derivative obtained in Synthesis Example 2 was dissolved in physiological saline, the volume was made 5 ml and the solution was filtered through a sterilized micropore filter. The filtrate was sealed in a sterilized umber glass bottle (type 1, 3 ml).

What is claimed is:

1. A superoxide dismutase derivative of the formula $$(SOD)(Z)_x$$

wherein (SOD) is a superoxide dismutase residue having 1 to 6 groups each derived from an amino group by removal of one hydrogen atom, (Z) is a monovalent copolymer residue comprising the following three units:

(a) a unit having the formula:

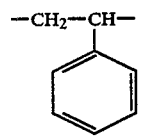

(b) a unit having the formula:

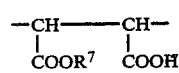

in which $R^7$ is a hydrogen atom or a butyl group, and (c) a unit having the formula:

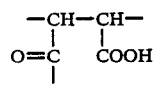

in which the carbonyl carbon atom of unit (c) is bound to (SOD) via a nitrogen atom of an amino group of (SOD), the copolymer residue having a weight-average molecular weight of 800 to 20,000, and x is an integer of 1 to 6 which corresponds to the number of the groups of (SOD) each derived from an amino group by removal of one hydrogen atom.

2. The superoxide dismutase derivative of claim 1 wherein the mole ratio of the constituent unit (a) to the constituent units (b) and (c), i.e. (a)/{(b)+(c)}, in the copolymer is substantially within the range of about 1 to about 1.3.

3. A method of producing a superoxide dismutase derivative of the formula (SOD) (Z)$_x$ wherein (SOD) is a superoxide dismutase residue having 1 to 6 groups each derived from an amino group by removal of one hydrogen atom, (Z) is a monovalent copolymer residue comprising the following three units:

(a) a unit having the formula:

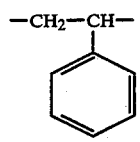

(b) a unit having the formula:

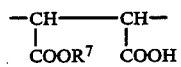

in which R$^7$ is a hydrogen atom or a butyl group, and (c) a unit having the formula:

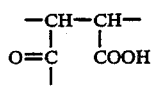

in which the carbonyl carbon atom of unit (c) is bound to (SOD) via a nitrogen atom of an amino group of (SOD), the copolymer residue having a weight-average molecular weight of 800 to 20,000, and x is an integer of 1 to 6 which corresponds to the number of the groups of (SOD) each derived from an amino group by removal of one hydrogen atom, which comprises reacting superoxide dismutase with a copolymer comprising the following three units:

(a) a unit having the formula:

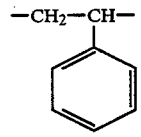

(b) a unit having the formula:

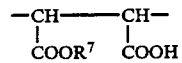

in which R$^7$ is a hydrogen atom or a butyl group, and (c) a unit having the formula:

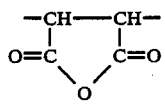

and having a weight-average molecular weight of 800 to 20,000, in an aqueous alkaline solution having a pH of 7 to 11.

4. The method of claim 1, wherein the superoxide dismutase is human superoxide dismutase or bovine superoxide dismutase.

5. The method of claim 3, wherein the human or bovine superoxide dismutase is a superoxide dismutase produced by genetic engineering techniques.

6. The method of claim 1, wherein the superoxide dismutase is human erythrocyte superoxide dismutase or bovine erythrocyte superoxide dismutase.

7. The method of producing a superoxide dismutase derivative of claim 1, where the mole ratio of the constituent unit (a) to the constituent units (b) and (c), i.e. (a)/{(b)+(c)}, in the copolymer is substantially within the range of about 1 to about 1.3.

8. The method of claim 1, wherein the copolymer is used in an amount of about 0.5 to about 30 moles per mole of superoxide dismutase.

9. The method of claim 1, wherein the aqueous alkaline solution is an aqueous solution of sodium carbonate, sodium hydrogen carbonate, sodium acetate or sodium phosphate.

10. The method of claim 1, wherein the reaction is carried out at a temperature of from about 3° C. to about 50° C.

11. A pharmaceutical composition for the prevention or treatment of an ischemic disease, said composition comprising an amount, effective for the prevention or treatment of an ischemic disease of a superoxide dismutase derivative of the formula (SOD) (Z)$_x$ wherein (SOD) is a superoxide dismutase residue having 1 to 6 groups each derived from an amino group by removal of one hydrogen atom, (Z) is a monovalent copolymer residue comprising the following three units:

(a) a unit having the formula:

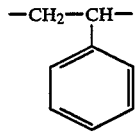

(b) a unit having the formula:

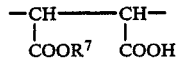

in which R$^7$ is a hydrogen atom or a butyl group, and (c) a unit having the formula:

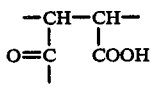

in which the carbonyl carbon atom of unit (c) is bound to (SOD) via a nitrogen atom of an amino group of (SOD), the copolymer residue having a weight-average molecular weight of 800 to 20,000, and x is an integer of 1 to 6 which corresponds to the number of the groups of (SOD) each derived from an amino group by removal of one hydrogen atom.

12. The pharmaceutical composition of claim 20 where the mole ratio of the constituent unit (a) to the constituent units (b) and (c), i.e. (a)/{(b)+(c)}, in the copolymer is substantially within the range of about 1 to about 1.3.

13. A method of preventing or treating an ischemic disease which comprises administering an effective amount for the prevention or treatment of an ischemic disease of a superoxide dismutase derivative of the formula (SOD) (Z)$_x$ wherein (SOD) is a superoxide dismutase residue having 1 to 6 groups each derived from an amino group by removal of one hydrogen atom, (Z) is a monovalent copolymer residue comprising the following three units:

(a) a unit having the formula:

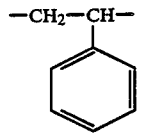

(b) a unit having the formula:

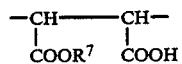

in which R$^7$ is a hydrogen atom or a butyl group, and (c) a unit having the formula:

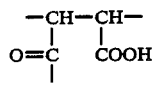

in which the carbonyl carbon atom of unit (c) is bound to (SOD) via a nitrogen atom of an amino group of (SOD), the copolymer residue having a weight-average molecular weight of 800 to 20,000, and x is an integer of 1 to 6 which corresponds to the number of the groups of (SOD) each derived from an amino group by removal of one hydrogen atom.

14. The method of claim 13 where the mole ratio of the constituent unit (a) to the constituent units (b) and (c), i.e. (a)/{(b)+(c)}, in the copolymer is substantially within the range of about 1 to about 1.3.

* * * * *